(12) United States Patent
Ley et al.

(10) Patent No.: US 8,475,847 B2
(45) Date of Patent: Jul. 2, 2013

(54) DESENSITISING AND REMINERALISING DENTAL COMPOSITION AS WELL AS DENTAL PARTICLES FOR THE COMPOSITION

(76) Inventors: Fritz Ley, Dernau (DE); Frederick Curro, Emerson, NJ (US); Heidi Albert, Tubingen (DE)

( * ) Notice: Subject to any disclaimer, the term of this patent is extended or adjusted under 35 U.S.C. 154(b) by 750 days.

(21) Appl. No.: 12/444,205

(22) PCT Filed: Oct. 2, 2007

(86) PCT No.: PCT/EP2007/060441
§ 371 (c)(1),
(2), (4) Date: Feb. 24, 2010

(87) PCT Pub. No.: WO2008/040723
PCT Pub. Date: Apr. 10, 2008

(65) Prior Publication Data
US 2010/0203092 A1    Aug. 12, 2010

(30) Foreign Application Priority Data

Oct. 4, 2006   (DE) .......................... 10 2006 046 952

(51) Int. Cl.
- *A61K 8/18* (2006.01)
- *A61K 9/68* (2006.01)
- *A61Q 11/00* (2006.01)

(52) U.S. Cl.
USPC ........... 424/724; 424/49; 433/215; 433/217.1

(58) Field of Classification Search
USPC ......................................................... 424/52
See application file for complete search history.

(56) References Cited

U.S. PATENT DOCUMENTS

| | | | |
|---|---|---|---|
| 3,175,951 A | 3/1965 | Tucker et al. | |
| 3,863,006 A | 1/1975 | Hodosh | |
| 3,888,976 A | 6/1975 | Mlkvy et al. | |
| 4,009,327 A | 2/1977 | Witt | |
| 4,048,300 A | 9/1977 | Tomlinson et al. | |
| 4,080,440 A | 3/1978 | DiGiulio et al. | |
| 4,362,713 A | 12/1982 | Buck | |
| 4,751,072 A | 6/1988 | Kim | |
| 4,923,683 A | 5/1990 | Sakuma et al. | |
| 4,990,327 A | 2/1991 | Neirinckx | |
| 5,037,639 A | 8/1991 | Tung | |
| 5,211,937 A | 5/1993 | Brandley et al. | |
| 5,270,031 A | 12/1993 | Lim et al. | |
| 5,437,857 A | 8/1995 | Tung | |
| 5,460,803 A | 10/1995 | Tung | |
| 5,534,244 A | 7/1996 | Tung | |
| 5,603,922 A | 2/1997 | Winston | |
| 5,858,333 A | 1/1999 | Winston | |
| 6,086,374 A | 7/2000 | Litkowski et al. | |
| 6,521,215 B2 | 2/2003 | Okay | |
| 6,733,818 B2 | 5/2004 | Luo et al. | |
| 6,846,500 B1 | 1/2005 | Luo et al. | |

FOREIGN PATENT DOCUMENTS

| | | |
|---|---|---|
| DE | 695 24 747 T2 | 8/2002 |
| DE | 103 30 204 A1 | 2/2005 |
| EP | 0 216 278 A2 | 9/1986 |
| WO | WO 00/59460 | 10/2000 |
| WO | WO 02/30380 A1 | 4/2002 |
| WO | WO 2005/002722 A1 | 1/2005 |

OTHER PUBLICATIONS

Search Report and Written Opinion Oct. 2, 2007.

*Primary Examiner* — Walter Webb

(57) ABSTRACT

The invention relates to a dental, particularly a remineralizing composition, effective for pain sensitive teeth, such as toothpaste, tooth powder, mouth wash, chewing gum, dental formulations or the like, comprising spherical dental particles having a particle size between 0.1 and 2 μm made of silica gel in an one-part combination, comprising at least one combination agent selected from at least a phosphate, a oxide, a further oxygen-containing compound, a hydroxide, hydrogen carbonate or carbonate of the metals of groups II and III of the periodic system, as well as zinc or tin, wherein the dental particles are present in an amount such that the $SiO_2$ amount resulting from the silica gel is less than 1 wt. %.

15 Claims, 2 Drawing Sheets

DESENSITISING AND REMINERALISING DENTAL COMPOSITION AS WELL AS DENTAL PARTICLES FOR THE COMPOSITION

CROSS-REFERENCE TO RELATED APPLICATIONS

This application claims priority to PCT/EP2007/060441, filed on Oct. 2, 2007; and German Application No. DE 10 2006 046 952.6, filed on Oct. 4, 2006.

FIELD OF THE INVENTION

The invention relates to a remineralising and desensitising dental composition in the form of, for example, toothpaste, tooth powder, mouthwash, chewing gum, therapeutic varnishes and the like. Furthermore, the invention relates to dental particles, for use in these compositions.

BACKGROUND OF THE INVENTION

The surfaces of teeth are in a constant balance between the loss and gain of minerals. This process is partially kept in balance by the chemical composition of saliva and the extracellular fluid. Disruption of the tooth surface integrity can occur by acidic food and beverages, bacterial challenge and erosion by exaggerated tooth brushing or grinding of the teeth.

These processes are accompanied by a demineralisation of the exposed tooth surfaces leading to clinical conditions such as dentine hypersensitivity and caries.

Enamel mainly consists of inorganic mineral substance (95% by weight=86% by volume). It does not consist of pure hydroxy apatite but of mixed apatite and defect apatite. In mixed apatite, calcium can be replaced by magnesium, strontium and other divalent cations. $PO_4^{3-}$ can be replaced by $HPO_4^{2-}$, $H_2PO_4^{2-}$, $CO_3^{2-}$ or $HCO_3$. In defect apatite, the location of calcium in the lattice remains empty.

In saliva, minerals like calcium and phosphates are dissolved. When pH drops in plaque and saliva, the dissolved phosphate ions are protonated and thus removed from the solution equilibrium. In order to re-establish the equilibrium, apatite crystals have to be dissolved from the enamel. Thus a demineralisation of the enamel (initial lesion) takes place. With raising pH, the reverse reaction occurs. Due to the over-saturation of the saliva with apatite, remineralisation takes place.

In an initial lesion immediately above the sound enamel, a translucent zone exists. It contains about 1% of pores. Sound enamel only contains about 0.1% of pores. These pores or micro-channels have a diameter of 0.5 to 1.5 μm and a depth of 100 μm, which eventually allow bacterial invasion.

Dentine or dentin is the tissue, situated beneath the enamel, that forms the major portion of a tooth. When challenged by demineralisation and bacteria, caries can result in enamel and dentine. Dentine hypersensitivity is a clinical condition defined by an exaggerated response of the pulpal nerve to stimuli like cold, sweet, etc. The basis of this condition is exposed dentine due to erosion of the enamel/cementum, due to gingival recession and/or periodontal surgery.

The mineral proportion of dentin represents only 70% by weight or 45% by volume. Dissolution of the dentin starts at a higher pH than the dissolution of enamel and it is much more porous. Therefore, caries spreads more rapidly upon reaching the dentin than in enamel. The body reacts with the formation of sclerosing dentin as an attempt to build a barrier between caries and pulp. Minerals are deposited in the tubules inhibiting the diffusion of acids, toxins and proteolytic enzymes as well as bacteria.

Many attempts have been made to treat dentine hypersensitivity. According to the prior art, one approach is to reduce the excitability of the pulp by changes of the chemical environment of the nerve. Therefore agents are used which make the tooth less sensitive. According to the prior art several nerve desensitising agents are known. For this purpose, predominantly potassium nitrate is used which is deployed in commercial toothpastes, for the desensitisation of teeth (U.S. Pat. Nos. 3,863,006, 4,009,327 and 4,751,072). In these patents, mainly formulation and compositions containing potassium salts, including potassium bicarbonate and potassium chloride, are described.

An additional attempt, according to the prior art, has been made to control dentine hypersensitivity by using agents obtunding the tubules partially or completely. These agents are described as tubule blocking agents. U.S. Pat. No. 4,990,327 discloses the desensitisation of teeth with strontium and fluoride ions. Furthermore, U.S. Pat. No. 3,888,976 discloses the treatment of sensitive teeth by using zinc and strontium ions. U.S. Pat. No. 5,211,937 discloses the use of charged polystyrene beads as a chemically inert agent which mechanically blocks the surface of tubules. U.S. Pat. Nos. 4,634,589 and 4,710,372 disclose the use of clays like laponite or hectorite to obtund the tubules. U.S. Pat. No. 5,270,031 discloses the use of polyacrylic acids with a typical molecular weight of approximately 450.000 to 4.000.000 used as tubule blocking agents. Furthermore, U.S. Pat. No. 4,362,713 discloses the use of water-soluble or water-swellable poly-electrolytes and their salts as tubule blocking agents.

Further, in the prior art, the use of substrates as spherical micro-particles is known, on which active therapeutic substances are adsorbed by chemical, electrostatic or ionic bonding, to accelerate the wound healing rate or bone regeneration. As a result, active chemical compounds can be released in a controlled way. These so-called micro-spheres can be hollow or massive; the chemical substance can be adsorbed on the surface or encapsulated within the sphere.

From U.S. Pat. No. 5,037,639, the use of amorphous, thus non-spherical calcium compounds is known, which are applied to the dentinal structure of the teeth reportedly leading to apatite formation in situ. This apatite formation reportedly leads to a remineralisation of the teeth and a reduction of hypersensitivity.

DE 695 24 747 T2 contains an extensive review of the prior art regarding the reduction of hypersensitivity with sub-micron particles and discloses the use of cationic charged colloidal particles in an aqueous environment. It is suggested, for example, to use commercially available non-spherical silica with an average particle size of 20 nm with a coating of aluminium oxide of 2 nm. This product consists of an aqueous, colloidal dispersion of the aluminium oxide-coated sub-micron particles. For dental compositions, the compound should be used on average in amounts of 0.1% to 10% by weight.

The thesis of Gerd Fischer entitled: "Development, Characterisation and Application of Novel Hybrid Materials" presented to the Faculty of Chemistry and Pharmaceutics of the Eberhard-Karls University of Tuebingen, 2004, describes the controlled synthesis of mono-disperse spherical silica particles with a diameter between 0.2 and 1.8 μm, according to the Sol-Gel-Process, and their combination with other materials. Among others, the coating and the co-condensation with hydroxyapatite, resulting in mono-disperse particles with diameters of between 1.5 and 3.5 μm is disclosed.

Within the combination, silica was used to generate shape and size whereas hydroxyapatite was used to introduce similarity to the dental material, for the restoration of enamel loss through the effect of the hydroxyapatite.

In EP 0 216 278 B1, the production of non-porous, mono-disperse spherical silica particles of the Sol-Gel Process, notably with a particle size of 0.05-10 µm is disclosed.

DE 103 30 204 A1 discloses a sol-gel-process for the preparation of non-porous, spherical, mono-disperse silica particles notably with a particle size between 0.2 and 1.2 µm, carrying molecules immobilised by so-called spacers at their surface.

Furthermore, WO 02/30380 A1 discloses the desensitisation of teeth by inducing a regeneration of bone materials to obtund the dentin tubules. Among others, the use of hydroxyapatite, fluoroapatite, chloroapatite, tricalcium phosphate and other substrates based on calcium phosphate is disclosed. These substances can be attached to a silica substrate with a particle size of the substrate <10 microns. The porous or non-porous particles carrying the desensitising agents are present in concentrations between 1% and 70% by weight in dental desensitising compositions like toothpaste, mouthwash, tooth powder, varnishes, chewing gum etc. The compositions may additionally contain typical ingredients like abrasives or additional desensitising or otherwise effective ingredients.

Disadvantageous, for all these agents for the desensitisation of teeth according to prior art, is that they only temporarily alleviate the symptoms without leading to a lasting obturation of open tubules by incorporation and remineralisation, i.e. crystal growth, since they are surface-acting only. Only a lasting occlusion of the tubules can prevent the occurrence of hypersensitive teeth.

These surface-acting substances according to the prior art are not able to achieve this. These substances penetrate the tubules insufficiently or not at all and cannot influence i.e. inhibit the nervous transmission. Because of the chemical structure of these substances they cannot be, or can only insufficiently be, incorporated into the existing tooth structure to generate a sufficient remineralisation of the teeth and an obturation of the tubules.

This not only applies for dentin but also for enamel. The prior art discloses a number of patents claiming remineralisation of enamel lesions and prevention of caries. U.S. Pat. No. 3,175,951 discloses, for instance, the use of fluorides to fight cavities.

In vitro and in vivo, it could be shown that initial lesions can be at least partly remineralised, and where applicable, even completely restored. Fluoride can influence the misbalanced interaction between de- and remineralisation in favour of remineralisation. Fluoride penetrates into the enamel by way of diffusion channels. In this way, fluoride is bound to the enamel forming fluoroapatite and fluoridated hydroxyapatite. In the outer layer of the enamel, less than 10% of the hydroxyl groups are replaced by fluoride, and in a depth of 50 µm, only 1% are replaced. While in saliva hydroxyapatite begins to be demineralised at a pH of 5.5. Fluoroapatite begins to demineralise in saliva at a pH of 4.6. Accordingly, in the presence of sufficient fluoride, remineralisation can begin to occur at a pH of 4.6 whilst without fluoride this occurs not until a pH 5.5.

Another method to promote remineralisation is the use of soluble calcium salts. U.S. Pat. No. 4,080,440 discloses the use of soluble calcium salts with soluble fluorides for the remineralisation of enamel. U.S. Pat. No. 4,048,300 discloses the use of calcium phosphates like fluoroapatite, fluorohydroxyapatite and hydroxyapatite as well as monofluorophosphate, carbonate and di-valent cations like zinc.

U.S. Pat. Nos. 6,733,818 and 6,846,500 combine amorphous calcium phosphate with casein-phosphopeptide and bicarbonate as chewing gums or confectionary. U.S. Pat. Nos. 5,858,333 and 5,603,922 disclose the use of products in dual chamber tubes, one chamber containing soluble calcium salts and the other chamber containing phosphates and fluoride, mixing upon simultaneous squeezing from the tube and leading to remineralisation in situ. U.S. Pat. Nos. 5,534,244, 5,437,857 and 5,460,803 disclose the use of amorphous strontium and calcium phosphates with or without fluoride for remineralisation of enamel. U.S. Pat. No. 6,521,215 discloses compositions and methods for bleaching and remineralisation of teeth, for treating hypersensitive teeth and for the treatment of caries, with a soluble calcium phosphate consisting of one or more compounds of the group monocalcium phosphate, tricalcium phosphate and tetracalcium phosphate. U.S. Pat. No. 4,923,683 discloses the use of micro-encapsulated hydroxyapatite and/or fluoride.

SUMMARY OF THE INVENTION

The present invention provides dental compositions and particles which can penetrate the tooth surface sufficiently to efficiently contribute to the remineralisation of the tooth structure of enamel and dentin and/or facilitate an obstruction of transport of matter and transmission of signals within the tubules and a subsequent desensitisation of the teeth by remineralisation and crystal growth within pores of the enamel as well as in dentin tubules and by blocking the tubules. As a result of remineralisation of dentine, hypersensitivity will be reduced and the original tooth structure will be maintained and/or restored after a cariogenic challenge. Through remineralisation of enamel through the precipitation of the dental particles on the surface and in the pores (micro-channels) of the enamel, the original tooth structure will be maintained and/or restored after a cariogenic challenge. This also prevents other dental disorders which are based on defects of the mineral structure like erosions for example.

Accordingly, in one aspect, the present invention provides a dental composition comprising non-porous, spherical particles, preferably mono-disperse, prepared by a combination in the form of a coating or co-condensation or mixture with a combination agent selected from at least one water insoluble phosphate of the metals of the II. and III. group of the periodic system, zinc and tin, or with at least one water insoluble oxygen containing compound, a hydroxide, a hydrogen carbonate or a carbonate of the same groups. The present invention further provides spherical, preferably non-porous silica particles preferably of defined uniform particle size. The present invention further provides therapeutically active dental particles of a particle size or diameter between 0.1 and 2 µm, preferably between 0.5 and 1.5 µm and with a $SiO_2$ amount—resulting from silica—below 1% by weight, preferably from 0.1 to 0.9% by weight and most preferably between 0.3 and 0.7% by weight. Water insoluble for the present invention means no absolute insolubility in water but only a slight solubility where under physiological conditions small amounts of ions can be released and delivered for the above described processes of remineralisation.

Additional benefits and advantages of the present invention will become apparent to those skilled in the art to which the present invention relates from the subsequent description of the preferred embodiment and the appended claims, taken in conjunction with the accompanying drawings;

DETAILED DESCRIPTION OF THE INVENTION

For the coating and the co-condensation the preparation of the dental particles is known. A further preparation method for the combination comprises mixing of the particles to form granules where preferably mono-disperse particles of silica are combined with mono-disperse particles of the phosphates, for example, of the same size, or a water insoluble oxygen containing compound, a hydroxide, a hydrogen carbonate or a carbonate, which are mixed, for example, in a granule-mixer. Particle sizes between 0.05 and 1.2 µm and preferably between 0.1 to 1.0 µm are mixed and granulated to form the dental particles.

Preferably, at least one apatite, preferably selected from the metals calcium, magnesium and strontium, and preferably hydroxyapatite, is combined with the silica particles to form the dental particles. Furthermore, the following phosphates like fluoroapatite, chloroapatite tricalcium phosphate and other compounds based on calcium phosphate, like monocalcium phosphate, tricalcium phosphate and tetracalcium phosphate are suitable. Further suitable combinations result from the following oxygen containing compounds for example, $MgO$, $SrO$, $BaO$, $Al_2O_3$, $ZnO$, $SnO$, $SnO_2$ and borates, aluminates, hydroxides, hydrogen carbonates and carbonates of these metals.

The dental particles, for example the hydroxyapatites, phosphates, oxygen containing compounds, hydroxides, hydrogen carbonates and carbonates-containing dental particles are contained in the finished dental composition in amounts of 0.1 to 10%, preferably from 1 to 5%. The dental particles contain the $SiO_2$ out of the silica in amounts of from 10% to 90%, preferably from 30% to 70%.

Missing proportions to add up to 100% in the dental particles may comprise the other above-mentioned desensitising agents like hydroxyapatite, strontium hydroxyapatite, magnesium hydroxyapatite or the other phosphates, the oxygen containing compounds, hydroxides, hydrogen carbonates and carbonates of the metals of the II. and III. group of the periodic system as well as zinc and tin.

Preferably particles are prepared with a bulk density between 1.0 and 4.0 g/cm$^3$ most preferably between 1.5 and 3 g/cm$^3$. Bulk density is determined according to DIN 53 912.

Figure 1:
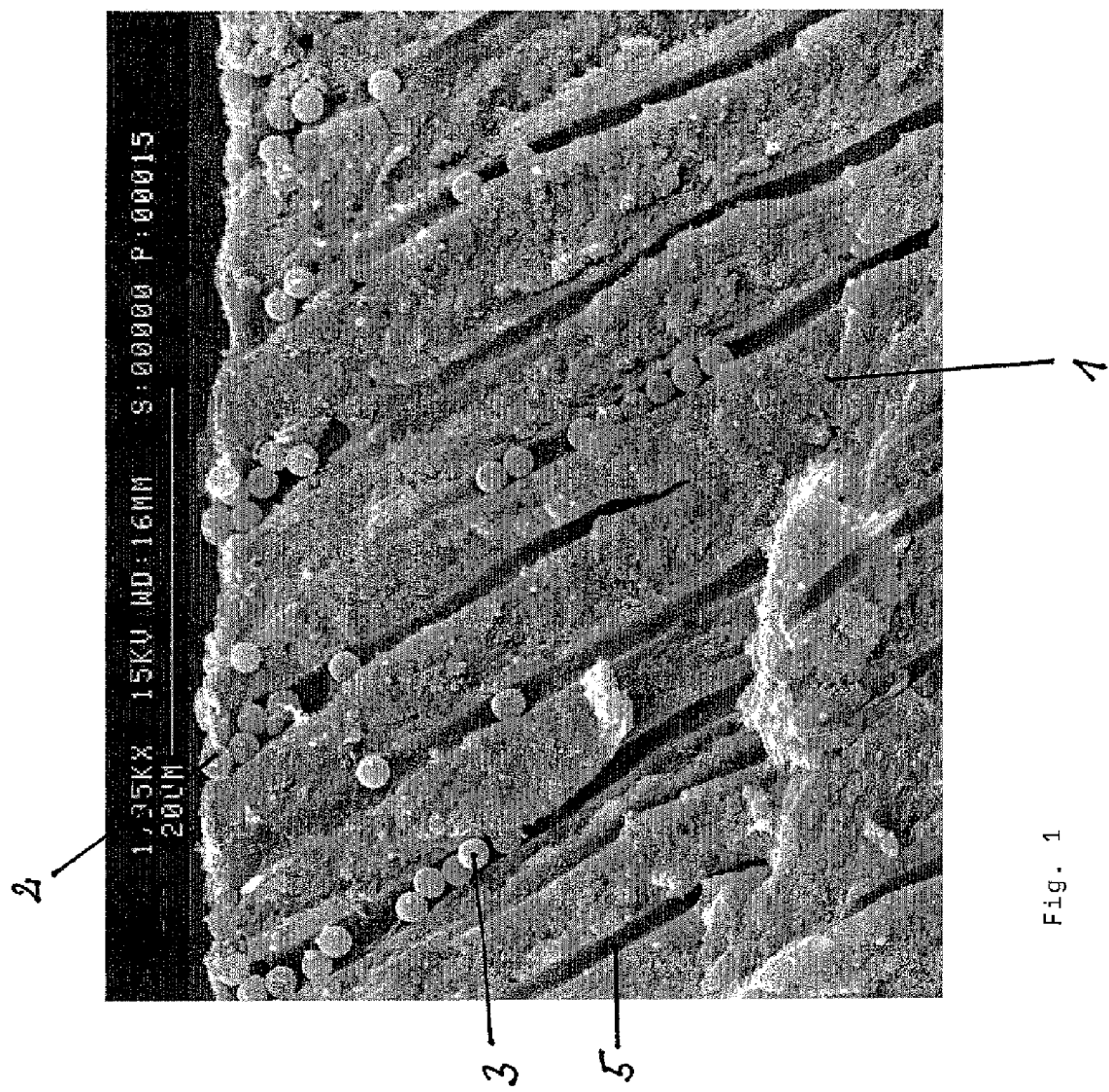
FIG. 1 shows a fracture of a dentin disc as well as dental particles according to the invention adhered and incorporated as well as tubules 5.
Figure 2:
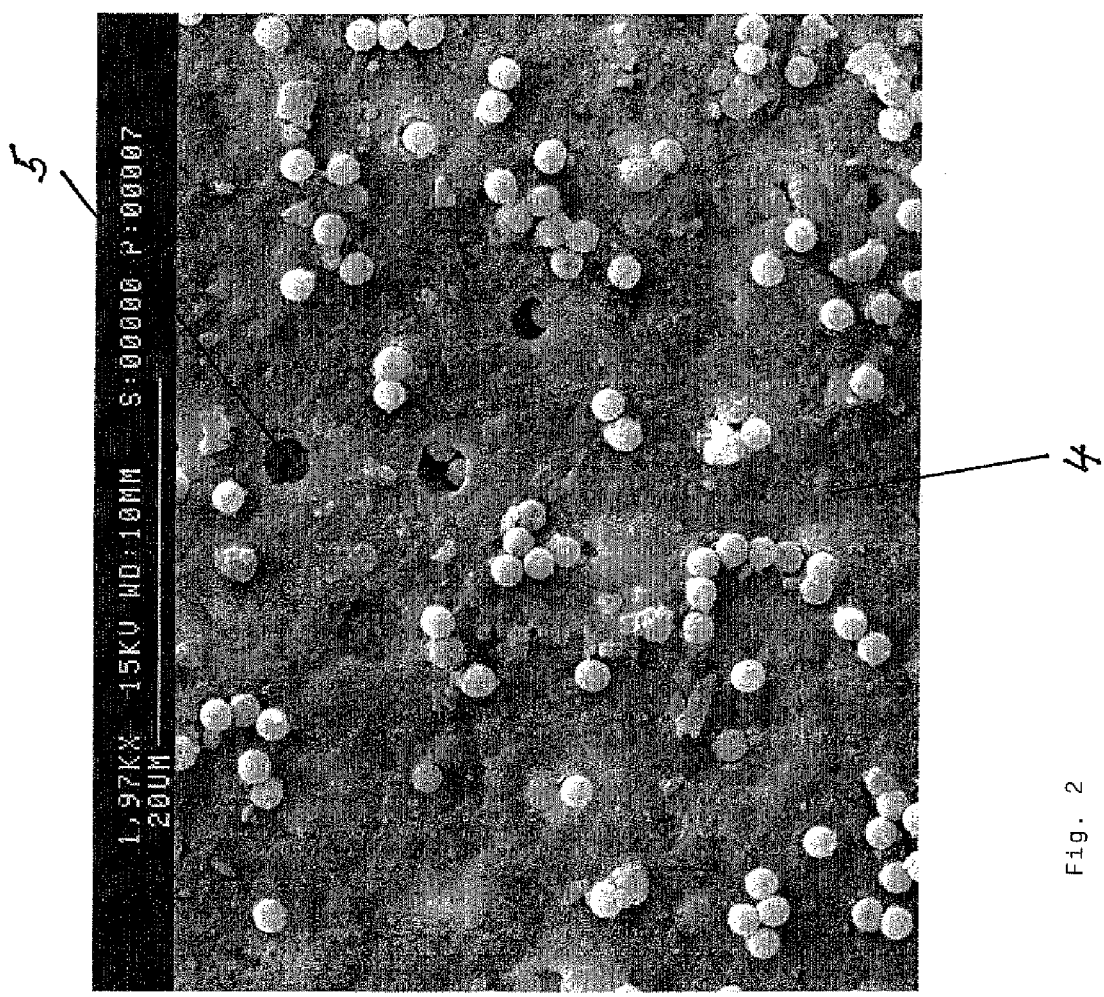
FIG. 2 shows a vertical view upon the surface of a dentin disc with patent tubules 5.

It has been shown that these dental compositions result in a regular adhesion or incorporation of the spherical dental particles onto or into the tooth surface, into the tooth structure or into the dentin tubules through an interaction between the silica with the combination material which cannot be achieved through the separate use of the phosphate or silica particles or in combination with other substrates. The regular adhesion or incorporation of the spherical particles as shown in FIGS. 1 and 2, occurs through the interaction with the surface charge of the tooth which is characterised by Van-der-Waals forces, ionic bonding and by the interaction with the surface charge of the tubules; the interaction with the extracellular dentinal fluid; and a combination of all three effects.

In each case a surprisingly strong immobilisation adhesion of the dental particles is a condition for the effect upon the damaged tooth structure.

The uniqueness of the charge of the spherical particles is caused by the geometry of the spheres producing a piezoelectric effect and by the ionic compounds combined with the $SiO_2$ particles making up the composition of the spheres.

Surprisingly, low concentrations of the silica i.e., less than 1% in the finished product optimizes the electrostatic interaction with the respective tooth surfaces. This is attributed to the geometry of the spherical particles producing an electrostatic effect whereby a higher concentration or proportion of silica diminishes the electrostatic interaction of the spheres with the tooth surfaces.

In addition to the electrostatic interaction, the cations present in the spherical particles serve as a reservoir or crystallisation nidus for the formation of cation dependent forms of hydroxyapatite. This cation dependency is seen with calcium being deposited preferably on the tooth surface whereas other cations such as Sr, Mg, being preferably deposited within the dentinal tubule.

The spherical particles are retained at the respective tooth surfaces by their inherent charges as described above. These spherical particles also fill voids in the enamel/dentine surface. Furthermore, a physical migration of the said spherical particles into the enamel pores and the dentinal tubules occurs. The spherical particles with their unique geometry and electrical charge adhere to, and are retained within the enamel pores and dentinal tubule. By being retained in the dentinal tubules, the spherical particles interact with the dentinal fluid by adsorbing it to their surface thereby inhibiting or reducing the dentinal fluid turnover rate. By reducing dentinal fluid flow due to changes on the surface from external sources, the odontoblastic cell body and its processes do not undergo a perturbation and subsequently do not trigger the nerve action potential.

The selection of the spherical dental particles best assures the densest packing to occlude the enamel pores and dentinal tubules when using spherical dental particles of different diameters according to the invention. This in addition to the above-mentioned favourable distribution of the electrical surface charge of the dental particles effects the desired immobilisation.

According to the invention, dental particles of different diameters may be combined for the dental compositions. Also according to the invention, dental particles which contain different combination agents in a dental composition can be used.

The particles are unique regarding density and geometry, providing penetration into pores and tubules, and also a certain retention time for the particle to act as a nidus for desensitising teeth as well as remineralising the tooth surface area to maintain surface integrity.

The different diameter and density of the spherical diameters are in line with different pore sizes of the dentine/enamel surface depending on the depth of penetration of the noxa, age of the individual and location of the tooth.

This invention differs from the prior art by the fact that the geometry of the particles as spherical particles as well as the range of the particle sizes can be optimised such that the different sizes of the pores and tubules within the tooth surface can be taken into account. The said particles can penetrate the tooth surface, thus achieving a retention time sufficient for the process of remineralisation and for achieving therapeutic efficacy.

While the above description constitutes the preferred embodiment of the present invention, it will be appreciated that the invention is susceptible to modification, variation, and change without departing from the proper scope and fair meaning of the accompanying claims.

The invention claimed is:

1. A dental desensitising and remineralizing composition for dental material for use as a toothpaste, tooth powder, mouthwash, chewing gum, or varnishes, the composition including spherical dental particles having a particle size between 0.1 μm and 2 μm, the dental particles consisting essentially of $SiO_2$ and at least one water insoluble combination agent capable of releasing ions under physiological conditions for remineralisation of the dental material, the combination agent chosen from at least one phosphate, oxide, hydroxide, hydrogen carbonate, or carbonate of the metals of group II or III of the periodic table, zinc, or tin;

wherein the $SiO_2$ from the dental particles is present in the composition in an amount ranging between 0.1% and 0.9% by weight of the composition.

2. The composition of claim 1 further comprising the amount of $SiO_2$ being between 0.3% and 0.7% of the composition.

3. The composition of claim 1 further comprising the particle size of the dental particles being between 0.5 μm and 1.5 μm.

4. The composition of claim 1 further comprising the combination of the dental particles obtained by coating, co-condensation or mixing and granulation of silica with the at least one combination agent formed of a phosphate, an oxide, a hydroxide, a hydrogen carbonate or a carbonate.

5. The composition of claim 1 further comprising the spherical dental particles being non-porous.

6. The composition of claim 1 further comprising the particles being mono-disperse.

7. The composition of claim 4 further comprising the particle size of the silica particles within the coated or mixed dental particles being between 0.05 μm and 1.5 μm.

8. The composition of claim 4 further comprising the particle size of the silica particles within the coated or mixed dental particles being between 0.1 μm and 1.0 μm.

9. The composition of claim 1 further comprising the particles being of the same or of different sizes within the composition.

10. The composition of claim 1 further comprising the silica particles being in a mono-disperse form or a mixture of different sizes.

11. The composition of claim 1 further comprising the phosphate being at least one apatite of the metals Ca, Mg, Sr, Ba, Al, B, Zn and Sn.

12. The composition of claim 11 wherein the apatite is a hydroxyapatite.

13. The composition of claim 1 further comprising the amount of silica in the dental particles being between 10% and 90% by weight of the particles.

14. The composition of claim 1 further comprising the bulk density of the dental particles being between 1.0 $g/cm^3$ and 4.0 $g/cm^3$.

15. The composition of claim 1 further comprising the bulk density of the dental particles being between 1.5 $g/cm^3$ and 3.0 $g/cm^3$.

* * * * *

UNITED STATES PATENT AND TRADEMARK OFFICE
CERTIFICATE OF CORRECTION

PATENT NO. : 8,475,847 B2  Page 1 of 1
APPLICATION NO. : 12/444205
DATED : July 2, 2013
INVENTOR(S) : Ley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1072 days.

Signed and Sealed this
Eighth Day of September, 2015

Michelle K. Lee
*Director of the United States Patent and Trademark Office*